(12) United States Patent
Groll

(10) Patent No.: US 9,218,453 B2
(45) Date of Patent: Dec. 22, 2015

(54) BLOOD GLUCOSE MANAGEMENT AND INTERFACE SYSTEMS AND METHODS

(75) Inventor: Henning Groll, Tucson, AZ (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1293 days.

(21) Appl. No.: 12/493,536

(22) Filed: Jun. 29, 2009

(65) Prior Publication Data

US 2010/0331651 A1 Dec. 30, 2010

(51) Int. Cl.
- *A61B 5/145* (2006.01)
- *G06F 19/00* (2011.01)
- *A61B 5/00* (2006.01)
- *A61B 5/042* (2006.01)

(52) U.S. Cl.
CPC ........ *G06F 19/3406* (2013.01); *A61B 5/14532* (2013.01); *A61B 5/7425* (2013.01); *A61B 5/7435* (2013.01); *A61B 5/7475* (2013.01); *G06F 19/323* (2013.01); *A61B 5/042* (2013.01); *A61M 2230/201* (2013.01)

(58) Field of Classification Search
CPC .. A61B 5/14532; A61B 5/7425; A61B 5/743; A61B 5/7435; A61B 5/7445; A61M 2230/201
USPC ................ 600/309, 345, 347, 365; 702/2–32; 715/730–732, 864
See application file for complete search history.

(56) References Cited

U.S. PATENT DOCUMENTS

| | | | |
|---|---|---|---|
| RE32,268 E | | 10/1986 | Gordon |
| 4,731,726 A | * | 3/1988 | Allen, III ...................... 600/300 |
| 4,999,482 A | | 3/1991 | Yang |
| 5,053,199 A | | 10/1991 | Keiser et al. |
| 5,251,126 A | | 10/1993 | Kahn et al. |
| 5,307,263 A | | 4/1994 | Brown |
| 5,352,351 A | | 10/1994 | White et al. |
| 5,366,609 A | | 11/1994 | White et al. |
| 5,424,035 A | | 6/1995 | Hones et al. |
| 5,438,271 A | | 8/1995 | White et al. |
| 5,463,467 A | | 10/1995 | Baumann et al. |
| 5,822,715 A | | 10/1998 | Worthington et al. |
| 5,889,585 A | | 3/1999 | Markart |
| 5,920,317 A | * | 7/1999 | McDonald ..................... 715/853 |
| 5,997,817 A | | 12/1999 | Crismore et al. |
| 6,055,060 A | | 4/2000 | Bolduan et al. |
| 6,366,295 B1 | * | 4/2002 | Kurashina ..................... 345/684 |
| 6,558,320 B1 | * | 5/2003 | Causey et al. ................. 600/300 |
| 6,641,533 B2 | | 11/2003 | Causey, III et al. |

(Continued)

FOREIGN PATENT DOCUMENTS

| | | |
|---|---|---|
| EP | 1 416 417 A2 | 5/2004 |
| WO | WO 2009/015497 A1 | 2/2009 |

OTHER PUBLICATIONS

Notification of Transmittal of the International Preliminary Report on Patentability, Sep. 9, 2011, 7 pages.

(Continued)

*Primary Examiner* — Navin Natnithithadha
*Assistant Examiner* — Meredith Weare
(74) *Attorney, Agent, or Firm* — Roche Diabetes Care, Inc.

(57) ABSTRACT

A blood glucose management device is operable to seamlessly provide a sequence of at least two displays of data relating to one or more blood glucose measurements to a user, upon minimal user interaction, with the blood glucose management device.

19 Claims, 10 Drawing Sheets

(56) References Cited

U.S. PATENT DOCUMENTS

| | | | |
|---|---|---|---|
| 6,645,368 B1 | 11/2003 | Beaty et al. | |
| 6,656,114 B1 | 12/2003 | Poulsen et al. | |
| 6,662,439 B1 | 12/2003 | Bhullar | |
| 6,840,904 B2 | 1/2005 | Goldberg | |
| 6,849,237 B2 | 2/2005 | Housefield et al. | |
| 6,906,802 B2 | 6/2005 | Voelkel | |
| 7,008,799 B1 | 3/2006 | Zimmer et al. | |
| 7,024,367 B2 | 4/2006 | Amano et al. | |
| 7,344,500 B2 | 3/2008 | Talbot et al. | |
| 2002/0023852 A1* | 2/2002 | Mcivor et al. | 206/305 |
| 2002/0170823 A1 | 11/2002 | Housefield et al. | |
| 2003/0125612 A1 | 7/2003 | Fox et al. | |
| 2004/0073464 A1 | 4/2004 | Huang | |
| 2004/0122476 A1 | 6/2004 | Wung | |
| 2004/0153257 A1* | 8/2004 | Munk | 702/31 |
| 2004/0186357 A1 | 9/2004 | Soderberg et al. | |
| 2005/0016844 A1 | 1/2005 | Burke et al. | |
| 2005/0020319 A1 | 1/2005 | Kim et al. | |
| 2005/0038332 A1* | 2/2005 | Saidara et al. | 600/347 |
| 2005/0096511 A1 | 5/2005 | Fox et al. | |
| 2005/0159656 A1 | 7/2005 | Hockersmith et al. | |
| 2005/0190280 A1* | 9/2005 | Haas et al. | 348/333.05 |
| 2005/0239156 A1* | 10/2005 | Drucker et al. | 435/14 |
| 2006/0229502 A1 | 10/2006 | Pollock et al. | |
| 2006/0248398 A1 | 11/2006 | Neel et al. | |
| 2006/0277048 A1 | 12/2006 | Kintzig et al. | |
| 2006/0286620 A1 | 12/2006 | Werner et al. | |
| 2007/0016449 A1 | 1/2007 | Cohen et al. | |
| 2007/0055799 A1 | 3/2007 | Koehler et al. | |
| 2007/0060871 A1 | 3/2007 | Istoc et al. | |
| 2007/0156033 A1 | 7/2007 | Causey, III et al. | |
| 2007/0213608 A1* | 9/2007 | Brown | 600/316 |
| 2007/0233395 A1 | 10/2007 | Neel et al. | |
| 2007/0255123 A1* | 11/2007 | Cummings et al. | 600/309 |
| 2007/0276197 A1* | 11/2007 | Harmon | 600/300 |
| 2008/0119705 A1 | 5/2008 | Patel et al. | |
| 2008/0133146 A1* | 6/2008 | Chang et al. | 702/23 |
| 2008/0172235 A1 | 7/2008 | Kintzig et al. | |
| 2008/0199894 A1 | 8/2008 | Galasso | |
| 2008/0243758 A1 | 10/2008 | Kintzig et al. | |
| 2009/0005651 A1 | 1/2009 | Ward et al. | |
| 2009/0113295 A1* | 4/2009 | Halpern et al. | 715/273 |
| 2009/0138207 A1 | 5/2009 | Cosentino et al. | |
| 2009/0149717 A1* | 6/2009 | Brauer et al. | 600/300 |
| 2009/0187351 A1* | 7/2009 | Orr et al. | 702/19 |
| 2009/0243808 A1 | 10/2009 | Vrba et al. | |
| 2010/0095229 A1* | 4/2010 | Dixon et al. | 715/763 |
| 2010/0184565 A1 | 7/2010 | Avellino | 482/9 |
| 2010/0331650 A1* | 12/2010 | Batman et al. | 600/365 |

OTHER PUBLICATIONS

U.S. Appl. No. 12/493,545, filed Jun. 29, 2009, Groll et al.

* cited by examiner

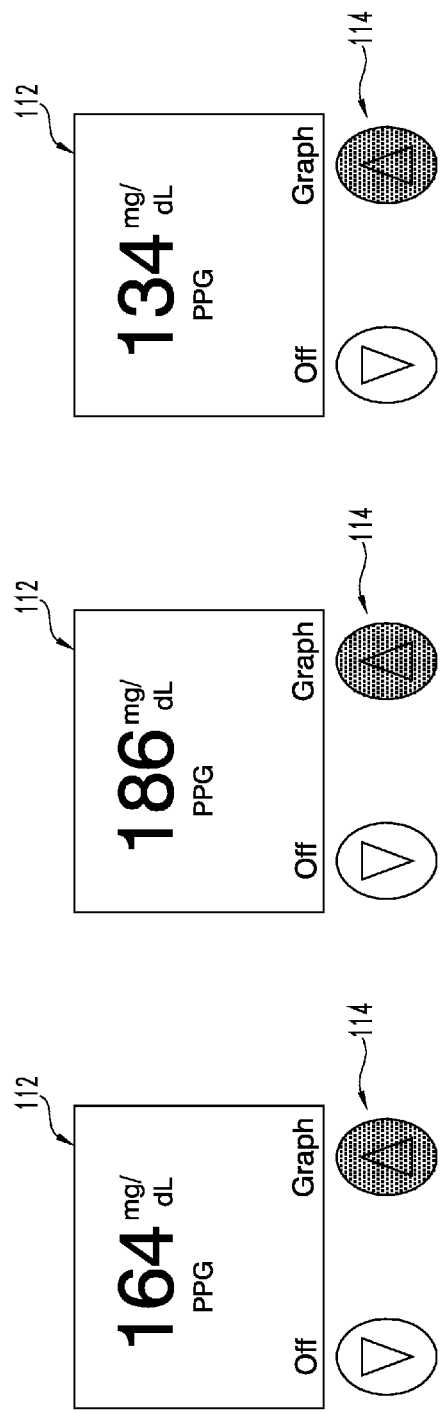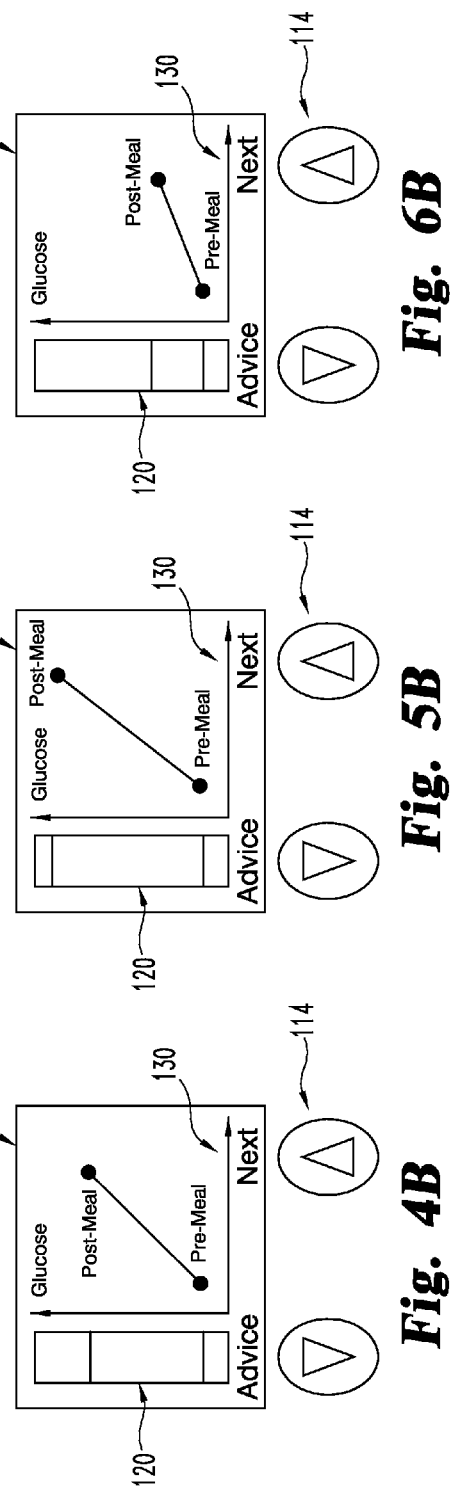
Fig. 4A  Fig. 5A  Fig. 6A
Fig. 4B  Fig. 5B  Fig. 6B

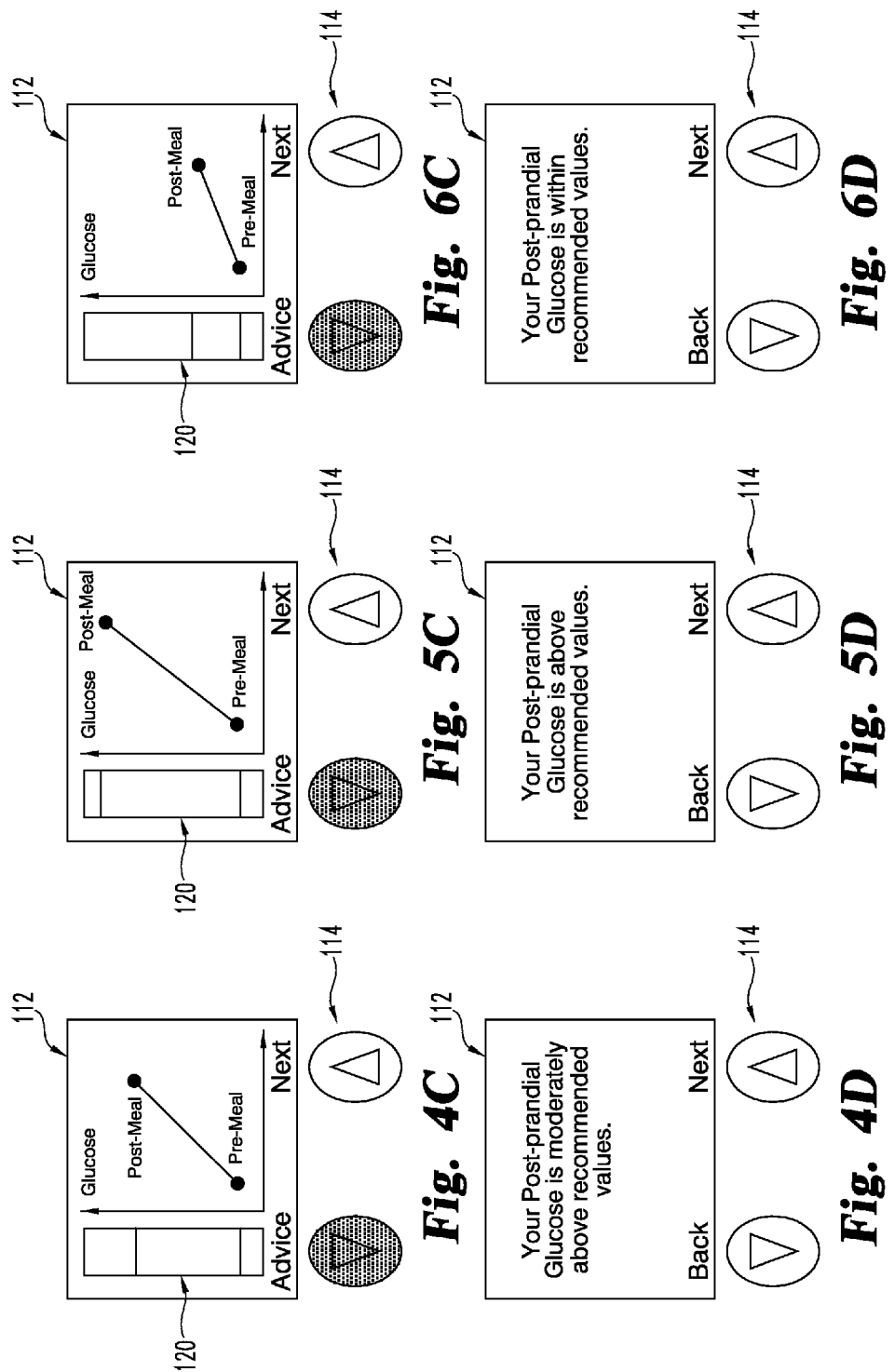

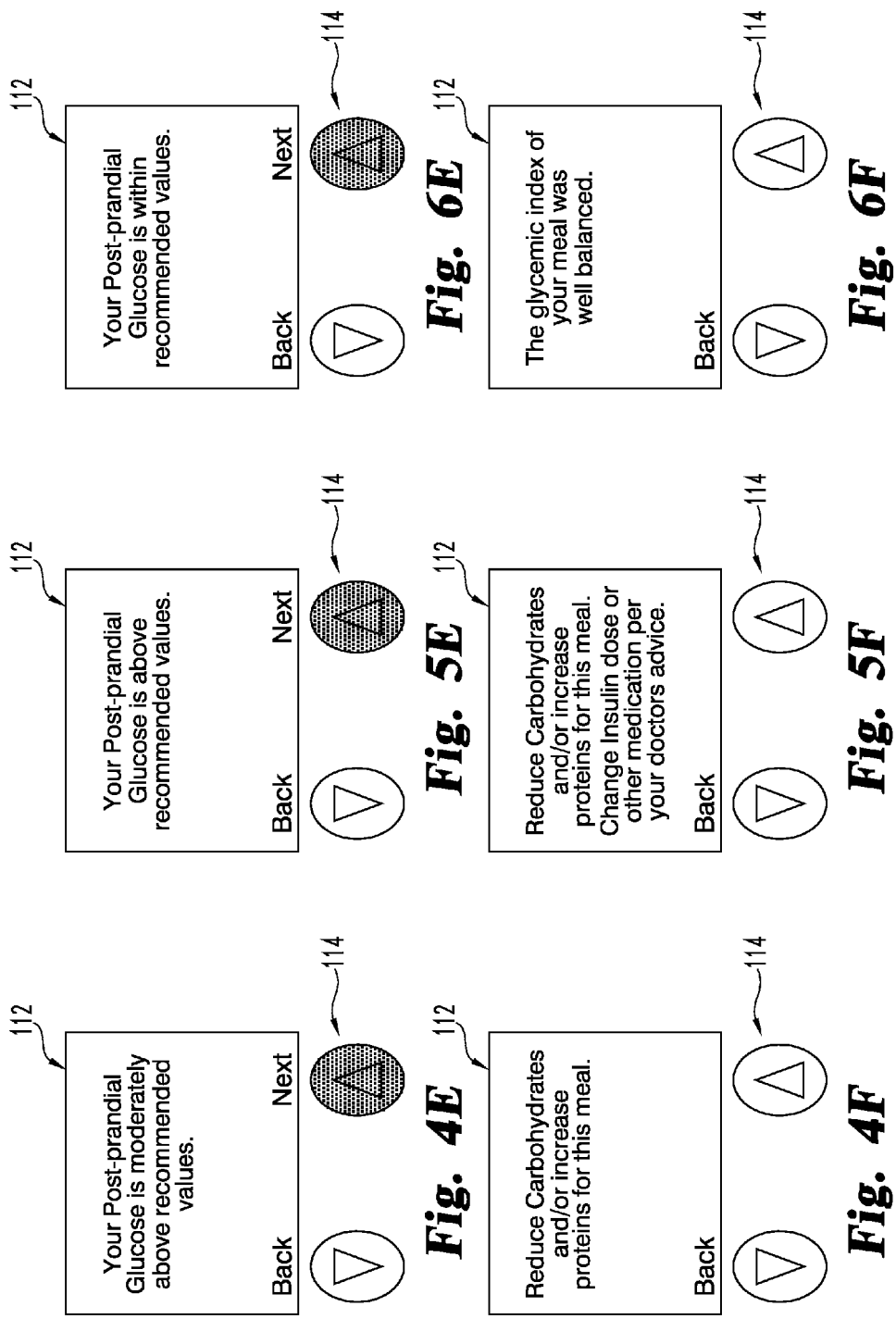

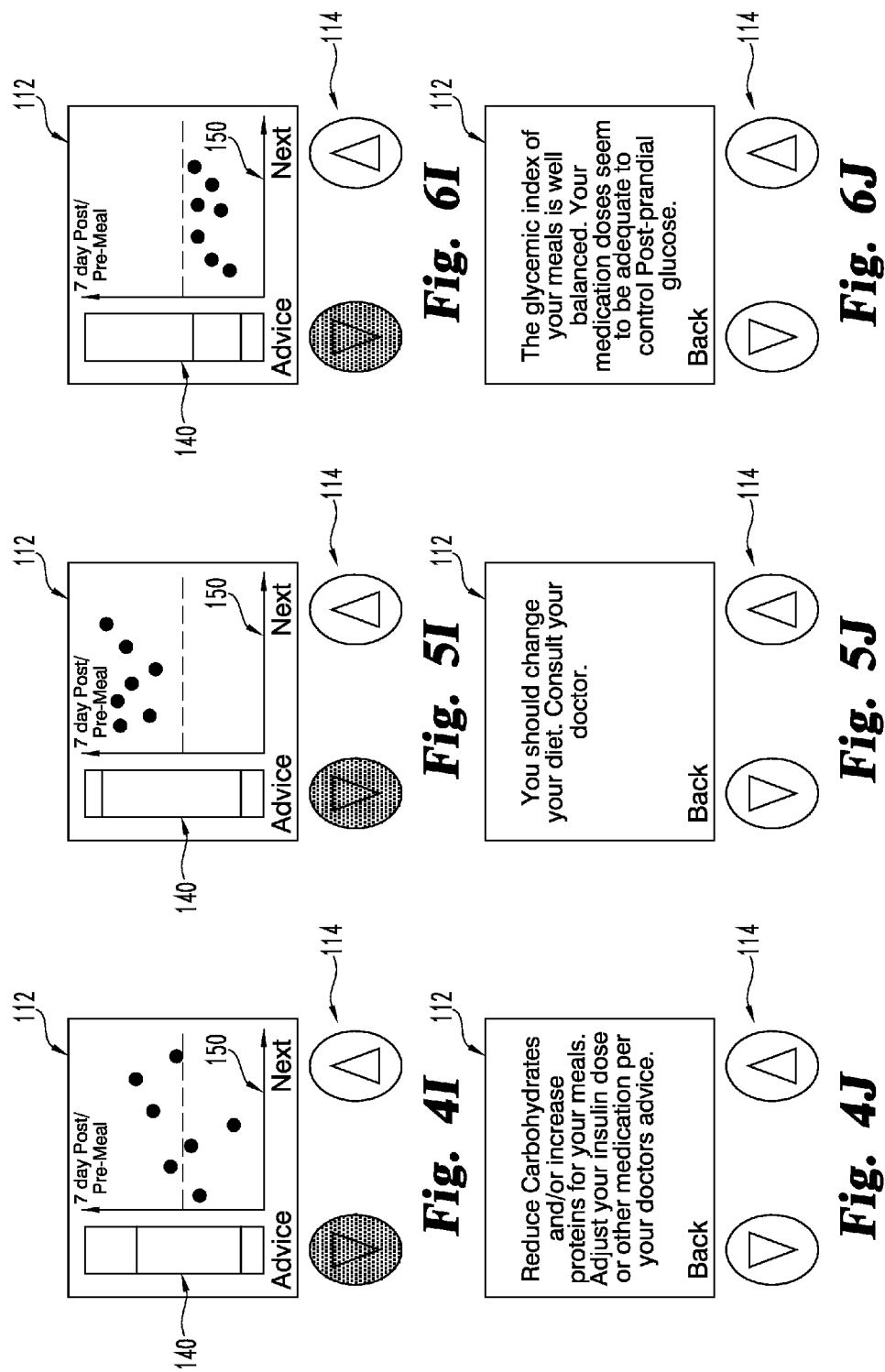

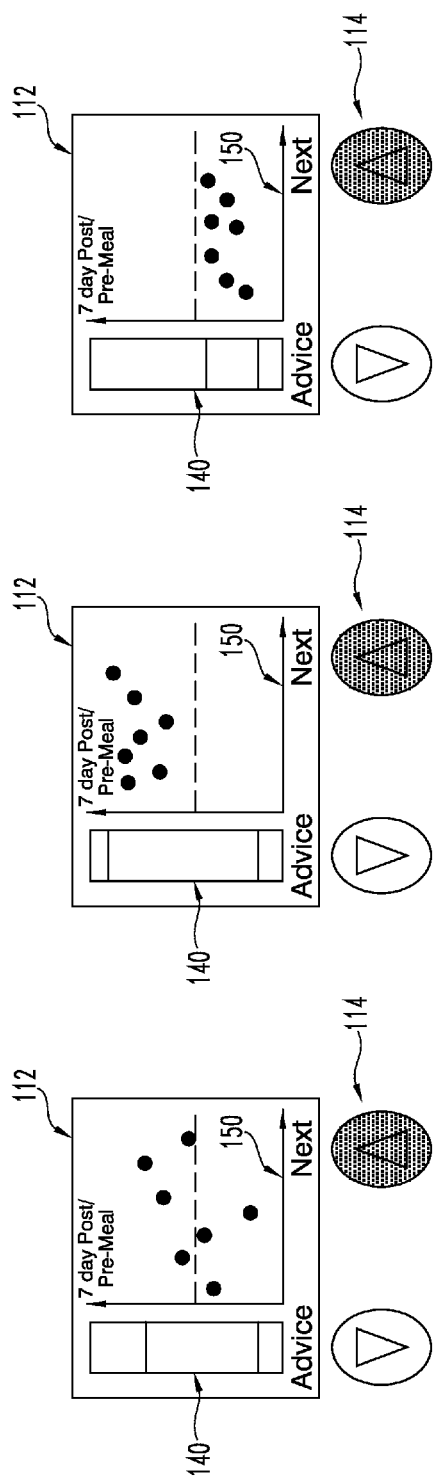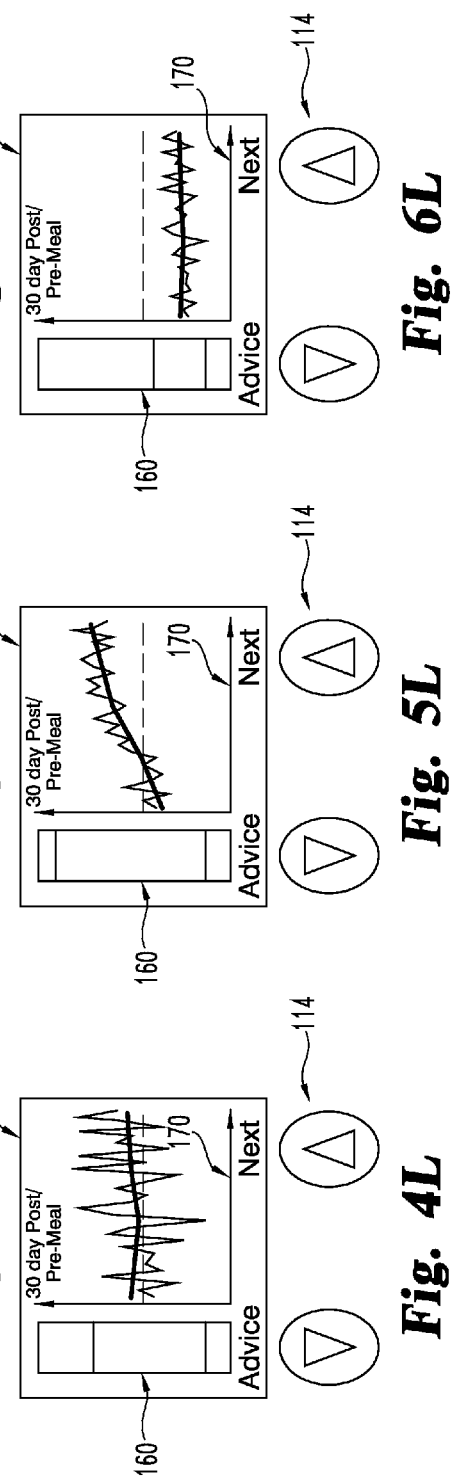

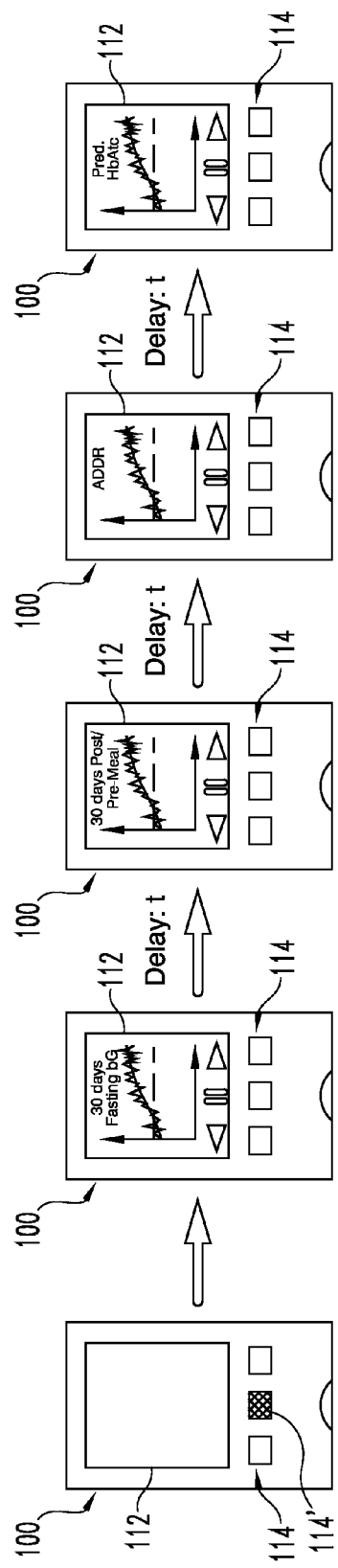

BLOOD GLUCOSE MANAGEMENT AND INTERFACE SYSTEMS AND METHODS

BACKGROUND

As the number of patients suffering from diabetes and similar medical conditions increases, self-monitoring of blood glucose wherein the patient monitors his or her blood glucose levels has become a common practice. The purpose of monitoring the blood glucose level is to determine the concentration level and then to take corrective action, based upon whether the level is too high or too low, to bring the level back within a normal range. The failure to take corrective action can have serious medical implications. Glucose monitoring is a fact of everyday life for diabetic individuals. Failure to test blood glucose levels properly and on a regular basis can result in serious diabetes-related complications, including cardiovascular disease, kidney disease, nerve damage and blindness.

People with diabetes who intensively manage their blood sugar experience long-lasting benefits. The Diabetes Control and Complications Trial (DCCT) was a clinical study conducted from 1983 to 1993 by the National Institute of Diabetes and Digestive and Kidney Diseases (NIDDK). The DCCT compared intensive to conventional treatments. Patients on intensive treatment kept glucose levels as close to normal as possible with at least three insulin injections a day or an insulin pump, and frequent self-monitoring of blood glucose. Intensive treatment aimed to keep hemoglobin A1c (HbA1c), which reflects average blood glucose over a 2- to 3-month period, as close to normal as possible. Conventional treatment consisted of one or two insulin injections a day with once-a-day urine or blood glucose testing. The results of the DCCT study showed that keeping blood glucose levels as close to normal as possible slows the onset and progression of eye, kidney, and nerve diseases caused by diabetes. In fact, it demonstrated that any sustained lowering of blood glucose helps, even if the person has a history of poor control.

A number of glucose meters are currently available that permit an individual to test the glucose level in a small sample of blood. Many of the meter designs currently available make use of a disposable test strip which in combination with the meter measures the amount of glucose in the blood sample electrochemically. In current glucose meters, the information displayed as a consequence of a successful blood glucose measurement is the respective blood glucose value and perhaps the time and date the measurement was performed. This information in combination with calculation of planned intake of carbohydrates or planned activities and knowledge of other situational or individual factors is in most cases sufficient to allow insulin dependent diabetics to adjust or derive the immediate dose of insulin to inject to control blood glucose level on the short-term.

Individuals can better manage insulin levels when a blood glucose measurement is considered in context with of other information relating to the activities of the individual. For example, individuals with diabetes may be asked to follow specific testing regimens, such as testing at specific times of day and before and after meals, in order to place a series of blood glucose measurements in context with various metabolic states or events for that individual. It is important for a person with diabetes to be aware of his or her blood glucose measurement one or two hours after a meal and compare it with a blood glucose measurement taken before a meal or compare it to a morning fasting blood glucose measurement to understand how a specific meal impacts blood glucose level. With this contextual information from prior blood glucose measurements, the individual can, for example, change the dosage of insulin, change the time of taking an insulin dose before a meal, or change the content of a meal, in order to maintain the post-meal blood glucose level within or below a recommended threshold. Other situations comparing one or more blood glucose measurements in context with one or more other blood glucose measurements and/or lifestyle events, such as exercise, sleep, fasting, snacking, meals, and insulin intake, for example, can assist the individual in better managing insulin levels.

Given the ramifications of accurate recording and reporting of blood glucose measurements, improvements in the apparatus and/or procedures to manage blood glucose are desired.

SUMMARY

A blood glucose management device is operable to seamlessly provide a sequence of at least two displays of data relating to one or more blood glucose measurements to a user. As used herein, seamlessly is defined as automatically without user interaction with the entry means or the blood glucose management device, or after a single user interaction with the entry means or blood glucose management device. The minimization of user interaction with the blood glucose management device to display blood glucose management data reduces the time and complexity currently associated with blood glucose management. For persons with diabetes the device enables blood glucose measurements to be placed in context with relevant lifestyle events and other blood glucose measurements to improve disease management abilities.

The portable blood glucose management device may or may not contain a blood glucose measurement system. In embodiments where the device includes a blood glucose measurement system, the device can be a blood glucose meter. For blood glucose management devices without a blood glucose measurement system, one or more blood glucose measurements stored in a blood glucose meter, personal computer, or other database or device can be transferred to the blood glucose management device via a data communications link or input into the device by the user. Examples of blood glucose management device employing a docking device are disclosed in U.S. patent application Ser. No. 12/493,545 titled Modular Diabetes Management Systems and filed on the same date as the subject application, the disclosure of which is incorporated herein by reference in its entirety. The blood glucose management device can be provided with operating logic, programmed or programmable to carry out the blood glucose management features herein or manufactured to include one or more microprocessors or other suitable devices operable to carry out the blood glucose management features herein. The blood glucose management features can be incorporated with one or more other devices such as a cellular telephone, smart phone, personal digital assistant, personal computer, or other portable device specifically dedicated to and configured to carry out the blood glucose management features herein.

In one aspect, a portable blood management device includes a housing with a display and a user entry means for receiving user input. A processor is in the housing operatively connected to the display and the user entry means, and a memory is connected with at least one processor. The processor is operable to produce on the display a representation of the blood glucose measurement that may be stored in the memory and to associate the blood glucose measurement with at least one other blood glucose measurement that may be stored in the memory. The processor is also operable to seamlessly produce a graphical representation on the display of the associated blood glucose measurements after producing the representation of the blood glucose measurement on the display.

In one refinement of the aspect the processor is operable to associate the blood glucose measurement with a context group including a plurality of blood glucose measurements associated therewith that may be stored in the memory. The processor is operable to seamlessly produce on the display a sequence of a plurality of graphical representations of blood glucose measurements in the context group.

In another refinement of the aspect the processor is operable to seamlessly produce on the display each of the plurality of graphical representations without user input to the entry means.

In another refinement of the aspect the processor is operable to seamlessly produce on the display contextual information directed to a currently displayed one of the graphical representations with or without user input into the entry means.

In another refinement of the aspect the advice includes an interpretation of the blood glucose measurements in the currently displayed graphical representation relative to pre-defined blood glucose limits.

In another refinement of the aspect the advice includes at least one of a recommended dietary change, a change in insulin dosage, and instructions to contact a physician or health care provider, for example.

In another refinement of the aspect the plurality of graphical representations includes xy-graphs of blood glucose measurements in the context group for seven day and thirty day time periods. In a further refinement, the plurality of graphical representations includes xy-graphs of blood glucose measurements in the context group for seven day, thirty day and ninety day time periods. In still a further refinement the plurality of graphical representations includes xy-graphs of blood glucose measurements in the context group for any one or more suitable time periods.

In another refinement of the aspect the processor is operable to seamlessly produce on the display advice directed to the associated blood glucose measurements upon user input to the entry means.

In another refinement of the aspect the graphical representation includes at least one of a bar chart and an xy-graph of the associated blood glucose measurements.

In another refinement of the aspect the entry means includes at least two buttons located adjacent to the display, and further wherein the processor is operable to assign a function to each of the at least two buttons and produce the assigned functions on the display, wherein the assigned functions depend on the graphical representation being currently produced on the display.

In another refinement of the aspect the memory includes a plurality of context groups of blood glucose measurements stored therein, the plurality of context groups including a prandial group, an exercise group, a fasting group, and a pre-sleep group. The prandial group may include one or more of breakfast, lunch, dinner and snack groups.

In another refinement of the aspect the processor is operable to seamlessly produce the graphical representation of the associated blood glucose measurement on the display automatically after the display of the representation of the blood glucose measurement for a period of time.

In another refinement of the aspect the processor is operable to seamlessly produce the graphical representation of the associated blood glucose measurement on the display upon a single user input to the user entry means during the display of the representation of the blood glucose measurement.

In another refinement of the aspect the entry means includes at least two buttons and the single user input consists of one press of one button of the entry means. In a further refinement of the aspect the entry means includes at least one button assigned to perform two or more functions and the single user input consists of one press of the at least one button of the entry means.

In another refinement of the aspect the entry means include a summary measurement data request and the processor is further operable to process a plurality of blood glucose measurements stored in a corresponding one of a plurality of context groups in the memory and seamlessly produce on the display a sequence of graphical representations of summary measurement data of the blood glucose measurements in each of the context groups.

In another refinement of the aspect the context groups for which summary measurement data is seamlessly displayed include at least two or more of a fasting context group, a prandial context group, an exercise context group, a pre-sleep context group, an episodic testing context group, a pre-office visit context group, a glucose tolerance context group, an Average Daily Risk Ratio context group, and a predicted HbA1c context group.

In another refinement of the aspect the processor is operable to seamlessly display the sequence of graphical representations by automatically displaying a next graphical representation in the sequence after displaying a current graphical representation for a period of time.

In another refinement of the aspect the means for inputting the blood glucose measurement includes a test strip port connected with the processor.

In a further aspect, a portable blood glucose management device includes a housing with a display and a user entry means for receiving user input. A processor is in the housing operatively connected to the display and the user entry means, and a memory is connected with the processor. Blood glucose measurements may be stored in a memory connected to the processor. The processor is operable to associate the blood glucose measurements that may be stored in the memory with a respective one of a number of context groups of blood glucose measurements. The processor further operates to seamlessly and sequentially produce on the display a plurality of graphical representations where each of the plurality of graphical representations is directed to blood glucose measurements in a different context group.

In one refinement of the aspect the housing includes a test strip port for providing a current blood glucose measurement to the processor.

In another refinement of the aspect the processor is operable to produce on the display a representation of the current blood glucose measurement and associate the current blood glucose measurement with at least one blood glucose measurement in one of the number of context groups of blood glucose measurements stored in the memory. The processor further is operable to seamlessly produce on the display a graphical representation of the associated blood glucose measurements after displaying the current blood glucose measurement.

In another refinement of the aspect the entry means include a summary measurement data request and the processor is operable to seamlessly and sequentially produce on the display the graphical representation of each context group of blood glucose measurements upon a single user input to the summary measurement data request.

In another refinement of the aspect the context groups for which summary measurement data is seamlessly produced include at least two or more of a fasting context group, a prandial context group, an exercise context group, a pre-sleep context group, an episodic testing context group, a pre-office visit context group, a glucose tolerance context group, an Average Daily Risk Ratio context group, and a predicted HbA1c context group.

In another refinement of the aspect the processor is operable to seamlessly produce the display of the sequence of graphical representations by automatically displaying a next graphical representation after displaying a current graphical representation for a period of time.

In another refinement of the aspect the processor is operable to display the next graphical representation without user input to the user entry means.

In another refinement of the aspect the processor is operable to pause the seamless and sequential display of the graphical representations upon user input to the user entry means.

In another aspect, a method for displaying blood glucose measurements includes: inputting a blood glucose measurement into a blood glucose management device; displaying the blood glucose measurement on the blood glucose management device; associating the blood glucose measurement with at least one other blood glucose measurement stored in the blood glucose management device; and seamlessly displaying a graphical representation of the associated blood glucose measurements on the blood glucose management device after displaying the blood glucose measurement.

In one refinement the aspect associates the blood glucose measurement with at least one context group of a plurality of blood glucose measurements stored in the blood glucose management device. It also seamlessly displays a sequence of a plurality of graphical representations of blood glucose measurements in the at least one context group on the blood glucose management device after displaying the graphical representation of the associated blood glucose measurements.

In another refinement of the aspect includes seamlessly displaying a sequence of a plurality of graphical representations of blood glucose measurement in a plurality of context groups of blood glucose measurements stored in the blood glucose management device.

In another refinement of the aspect the plurality of context groups include a prandial group, an exercise group, a fasting group, and a pre-sleep group.

In another refinement of the aspect the context groups are segregated based on a time of day of the blood glucose measurements associated therewith.

In another refinement the aspect seamlessly displays the graphical representation occurs upon a single user interaction with a user entry means of the blood glucose management device.

In another refinement the aspect seamlessly displays the graphical representation occurs automatically after a period of time of displaying the blood glucose measurement and without any user interaction with an entry means of the blood glucose management device.

In another refinement the aspect seamlessly displays the graphical representation includes simultaneously displaying a bar graph and an xy-chart of the associated blood glucose measurements.

In another refinement the aspect includes assigning and displaying at least two functions to entry means of the blood glucose management device while seamlessly displaying the graphical representation of the associated blood glucose measurements.

In another refinement of the aspect one of the at least two functions provides an input to seamlessly display advice regarding the associated blood glucose measurements and the other of the at least two functions provides an input to seamlessly display a second graphical representation of the blood glucose measurement with an associated context group that includes a plurality of blood glucose measurements over time stored in the blood glucose management device.

In another refinement of the aspect the advice includes an interpretation of the blood glucose measurements relative to pre-defined blood glucose limits.

In another refinement of the aspect the advice includes a recommended dietary change.

In another aspect, a method for displaying blood glucose measurements includes: storing a plurality of blood glucose measurements in a memory of a blood glucose management device; associating each of the plurality of blood glucose measurements with one of a number of context groups stored in the memory; and seamlessly displaying a sequence of at least one graphical representation of each of the number of context groups with its associated blood glucose measurements on a display of the blood glucose management device upon input to the blood glucose management device of a request for summary measurement data.

In one refinement the aspect includes automatically displaying the graphical representation of a next one of the context groups after a current graphical representation is displayed for a period of time.

In another refinement the aspect includes pausing the automatic sequential display of the graphical representations by engaging an entry means of the blood glucose management device.

In another refinement the aspect includes re-displaying at least one previously displayed graphical representation by interfacing with entry means of the blood glucose management device.

In another refinement the aspect includes resuming the seamless display of the sequence of at least one graphical representation of each context group after re-displaying the at least one previously displayed graphical representation.

In another refinement of the aspect the context groups for which summary measurement data is seamlessly displayed include a fasting context group, a prandial context group, an Average Daily Risk Ratio context group, and a predicted HbA1c context group.

In another refinement the aspect seamlessly displays the sequence of at least one graphical representation of each context group consists of pressing a button on the blood glucose management device.

BRIEF DESCRIPTION OF THE FIGURES

FIGS. 8A-8E show a series of displays on the blood glucose management device that seamlessly and sequentially advance to allow the user to view summary measurement data for a plurality of context groups of blood glucose measurements.

DETAILED DESCRIPTION OF THE ILLUSTRATED EMBODIMENTS

Figure 1:
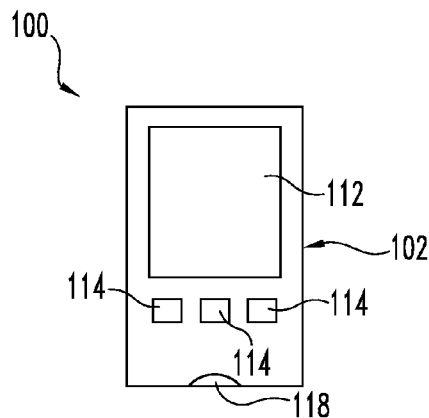
FIG. 1 illustrates one embodiment of a blood glucose management device.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In order to control and more effectively adjust the therapy, level of activity and lifestyle to achieve optimum glycemic control, diabetics and their health care providers need information based on more than one blood sugar measurement. For example, a series of fasting blood glucose values taken over multiple days and related trends, variability, ruining or absolute averages can provide help in adjusting behavior as well as medication for both insulin and non-insulin dependent diabetics.

Referring to FIG. 1 there is shown a device such as a blood glucose (bG) management device 100 for managing blood glucose levels in the blood of an individual. The bG device 100 includes a housing 102 with a capable display 112 and a user entry means 114. In some embodiments, bG device includes a test strip port 118, but in other embodiments does not. For embodiments with test strip port 118, electronic circuitry is contained within housing 102 to provide a measurement of a glucose level from a sample of blood on a test strip in or presented at test strip port 118. Other embodiments contemplate other suitable means for obtaining blood glucose measurements, including blood glucose meters where the test strip is integrated into the meter, and bG devices 100 where blood glucose measurements are entered by the user into the device and/or transferred to bG device 100 from another memory or database, such as the modular device disclosed in U.S. patent application Ser. No. 12/493,545 titled Modular Diabetes Management Systems, where the modular device therein includes a docking device that is the "bG device 100" herein, and the memory from which the measurements are obtained is a bG meter docked to the docking device. Housing 102 can be sufficiently compact so that it can be conveniently hand held and carried by the user, or, as in the case of a bG device 100 comprising a component of a modular system, a hand-held blood glucose meter can be carried entirely within housing 102. The bG device 100 may also include one or more other compartments or features for storage of other peripheral components usable with bG device 100, such as lancets, test strips, navigation pens used to navigate and interact with display 112, or other devices (not shown) which may be useful with bG device 100.

Figure 2:
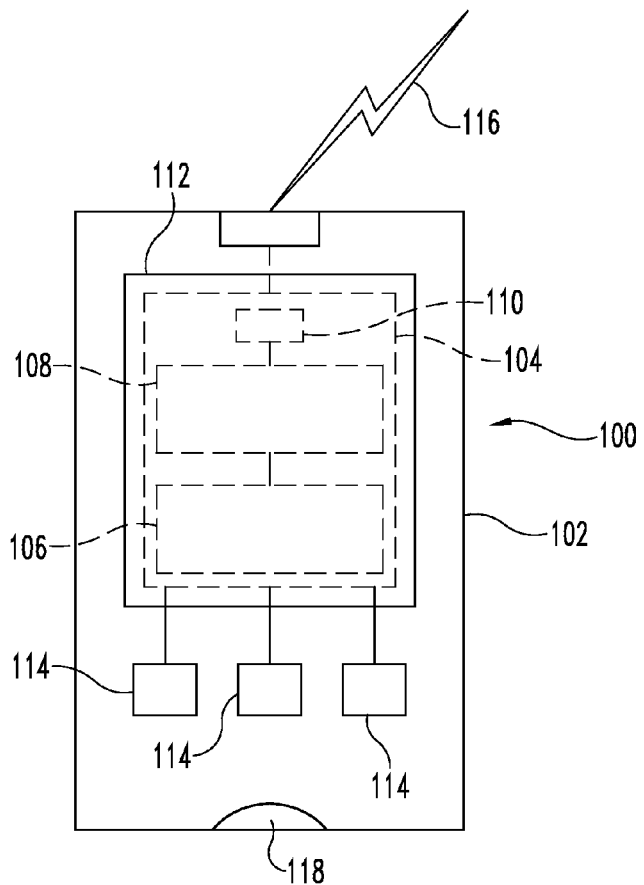
FIG. 2 illustrates a schematic of the blood glucose management device of FIG. 1.

In FIG. 2 there is shown one embodiment of a schematic of bG device 100. The bG device 100 includes hardware 104, including a memory 106 associated with at least one processor 108 that is connected with memory 106, and a real-time clock 10 associated with memory 106 and connected with the at least one processor 108. Display 112 is connected directly or indirectly with processor 108 with, for example, a display driver, and operable to provide a user readable display of output from processor 108. User entry means 114 is connected with processor 108 and accessible by the user to provide input to processor 108. Processor 108 is further configured or programmed to process bG measurements stored in memory 106 and produce a representation of the processed bG measurements on display 112. Processor 108 is further configured or programmed to receive input commands from user entry means 114 and provide an output that responds to the input commands. Processor 108 may also receive input from other computing or memory storage device.

It is contemplated that bG measurement data may be input directly into memory 106 via entry means 114 or input therein from another bG meter, computer or storage device via a communications link 116. For embodiments where bG device 100 is a blood glucose meter with a test strip port, processor 108 is connected with test strip port 118 and operable to process and record data in memory 106 relating to a blood glucose measurement taken in test strip port 118 and produce a representation of the current bG measurement and associated data on display 112.

Hardware 104 may be comprised of one or more components configured as a single unit or of multi-component form. Components of hardware 104 may be programmable, a state logic machine or other type of dedicated hardware, or a hybrid combination of programmable and dedicated hardware. One or more components of hardware 104 may be of the electronic variety defining digital circuitry, analog circuitry, or both. As an addition or alternative to electronic circuitry, hardware 104 may include one or more mechanical or optical control elements.

In one embodiment including electronic circuitry, hardware 104 includes an integrated processor 108 operatively coupled to one or more solid-state memory devices defining, at least in part, memory 106. Memory 106 may contain operating logic to be executed by a processor 108 that is a microprocessor and is arranged for reading and writing of data in memory 106 in accordance one or more routines of a program executed by microprocessor 108. Alternatively or additionally, processor 108 may utilize a Digital Signal Processor (DSP) and/or Application Specific Integrated Circuit (ASIC), and/or discrete, dedicated logic components corresponding to the components schematically represented in FIG. 2 associated with meter. Other embodiments are contemplated that include multiple processors 108. For example, one processor 108 is used in measuring a blood glucose value, and a second processor is used to manage the user interface and memory of bG device 100.

Memory 106 may include one or more types of solid-state electronic memory and additionally or alternatively may include the magnetic or optical variety. For example, memory 106 may include solid-state electronic Random Access Memory (RAM), Sequentially Accessible Memory (SAM) (such as the First-In, First-Out (FIFO) variety or the Last-In First-Out (LIFO) variety), Programmable Read Only Memory (PROM), Electrically Programmable Read Only Memory (EPROM), or Electrically Erasable Programmable Read Only Memory (EEPROM); mask Read Only Memory; or a combination of any of these types. Also, memory 106 may be volatile, nonvolatile or a hybrid combination of volatile and nonvolatile varieties. Some or all of memory 106 can be of a portable type, such as a disk, tape, memory stick, cartridge, or the like. Memory 106 can be at least partially integrated with processor 108 and/or may be in the form of one or more components or units.

Besides memory 106, hardware 104 may also include clock 110, display 112, and entry means 114 associated therewith, along with signal conditioners, filters, limiters, Analog-to-Digital (A/D) converters, Digital-to-Analog (D/A) converters, communication ports, or other types of operators as would occur to those skilled in the art to implement the present invention. Entry means 114 may include one or more input devices like a push-button, keyboard, mouse or other pointing device, touch screen, touch pad, roller ball, or a voice recognition input subsystem. Display 112 may include one or more output means like an operator display that can be of a Cathode Ray Tube (CRT) type, Liquid Crystal Display (LCD) type, plasma type, Organic Light Emitting Diode (OLED) type, a printer, or the like. The display can be monochrome or color. Other input and display means can be included such as loudspeakers, voice generators, voice and speech recognition systems, haptic displays, electronic wired or wireless communication subsystems, and the like.

Housing 102 may include a communications link 116 for wired or wireless connection with a secondary device, such as a personal computer, diabetes management device, bG meter, personal digital assistant, cellular telephone, modem, local area network, or the worldwide web for viewing and/or analysis of bG measurement data stored in memory 106. The bG measurements stored in memory 106 of bG device 100 can be transferred to the secondary device when communication is established, or blood glucose measurements can be transferred to memory 106 of bG device 100 when communication is established. In addition, data in the form of executable programs, previously transferred bG measurement data, and other information can be transferred from a secondary device to memory 106 for processing by processor 108.

Figure 3:
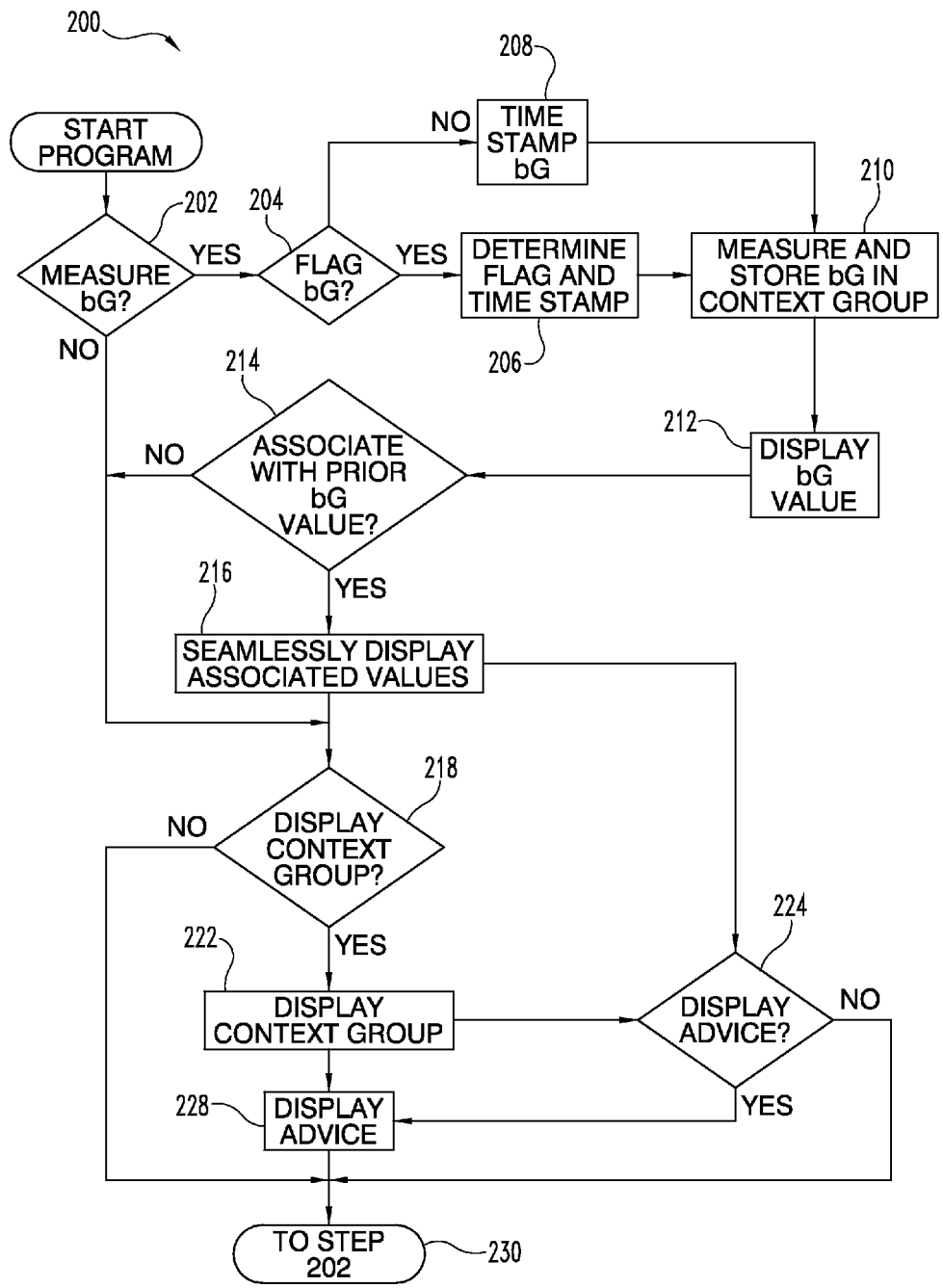
FIG. 3 is a flowchart illustrating steps executable by the blood glucose management device of FIG. 1 to seamlessly provide to the user data regarding blood glucose measurements stored in the blood glucose management device in a sequence of two or more displays on the blood glucose management device.

Referring to FIG. 3, a flow chart 200 illustrates steps of operation by processor 108, either through a program stored therein or by operating logic of dedicated hardware of bG device 100, so that bG device 100 seamlessly produces on display 112 graphical and/or textual representations of bG measurements in one or more context groups of bG measurements stored in memory 106. In step 202, processor 108 determines if the user wants to input a bG measurement. The user can affirmatively address this query by inputting a bG measurement. For bG devices including bG meter functionality, the query can be addressed by simply inserting a test strip into test port t18, or by pressing an activation button that causes the bG meter to present a test strip to which a blood sample is then applied, and the bG meter will then proceed to process the blood sample for the bG measurement. Alternatively, a query can be displayed on display 112 and the user can indicate whether or not a bG measurement is to be directly entered by the user with entry means 114 or by transfer from communications link 116. If no bG measurement entry is desired, the routine continues at step 218, discussed further below.

In one embodiment, processor 108 automatically provides an input screen at step 202 to allow the user to enter a blood glucose measurement. The user can then directly enter a measured blood glucose value directly into bG device 100. In one example, the display screen provides a display value of, for example, 0.0 or X.Y, where X.Y is equal to the last entered blood glucose measurement, or the last blood glucose measurement entered at that particular time of day. The user enters the blood glucose measurement through changing the X.Y values up or down by manipulating buttons of entry means 114. Alternatively, bG device 100 is operable to automatically retrieve a bG measurement from an insulin dosing device, such as an insulin pen or pump, or from a blood glucose measurement device.

In one embodiment, entry means 114 includes no more than two press-to-enter type buttons, that are each multi-functional since the function of the buttons varies during the execution of the routine. Display 112 provides an indication to the user of the respective function of each button of entry means 114 based on the particular step in the routine at which processor 108 is operating. The user can then direct the operation of processor 108 by selecting and interfacing with the button that provides the desired functionality. Other embodiments contemplate entry means 114 with only one button, only three buttons, or four or more buttons. In still other embodiments, entry means 114 includes a voice command feature, a stylet, touch-pad, a single directional button or key that executes a command depending on the side or location of the button pressed, a mouse with a pointer to electronically select or a stylet to directly touch an icon on display 112 to provide the desired input to processor 108.

Referring back to flow chart 200, if the user desires to input a bG value at step 202, then the user may be queried at step 204 whether or not to flag the bG measurement. The bG measurement can be flagged so that it is associated with an appropriate context group of bG measurements stored in memory 106. The context groups of bG measurements can be determined based on any one or more lifestyle events of the user. Furthermore, the association of a particular bG measurement with a particular context group can be based on a time-of-the-day of the measurement, a user set flag, or an automatically set flag.

Various context groups of bG measurements are contemplated for storage in memory 106. The context groups may include pre-prandial and post-prandial bG measurements, pre-exercise and post exercise bG measurements, fasting bG measurements, pre-sleep or bedtime bG measurements, or any other context group relating to the lifestyle of the user. The context group may also be based on a specific pre-defined testing sequence of bG measurements stored or loaded into memory 106, such as a Glucose tolerance tests, pre-office visit tests, or episodic tests. Another context group includes bG measurements over a pre-defined time that includes all bG measurements stored in memory 106 of bG device 100. Other context groups are contemplated in which bG measurements are grouped in a range of time-of-the-day measurements, such as those related to mealtimes. For example, range of time-of-day context groups can be established for 4 a.m.-8 a.m. to coincide with breakfast, 11 a.m.-1 p.m. to coincide with lunch, 3 p.m.-5 p.m. to coincide with dinner, and 6 p.m.-10 p.m. to coincide with a pre-sleep snack. If the bG measurement is to be flagged and associated with a context group, flow chart 200 continues at step 206 so that the flag associated with the bG measurement to be taken is either set by the user or set according to pre-programmed parameters for flagging the bG measurement. A time stamp from clock 10 can also be associated with the bG measurement so that the time and date of the bG measurement is stored in memory 106 along with the bG measurement.

As discussed above, it is contemplated that one or more context groups are established for the bG measurements taken within certain timeframes. For example, if a user set flag is not associated with the bG measurement, the routine proceeds from step 204 to step 208, or to step 208 directly from step 202, where a time stamp from clock 10 is associated with the bG measurement so that the time and date of the bG measurement is stored in memory 106. The routine then continues from either step 206 or step 208 where the blood glucose level is received and stored in memory 106 in its proper context group of other bG measurements in that time frame. Furthermore, it is contemplated that a bG measurement can be associated with multiple context groups. For example, a bG measurement may be flagged as a pre-prandial or post-prandial measurement, and is therefore associated with the prandial context group. The bG measurement also has a time stamp and can be associated with and stored within the respective time-of-day context group.

In addition to providing context group information relating to a blood glucose measurement, the user can be guided seamlessly or automatically through a series of one or more screens on display 112 to input contextual information relative to lifestyle events or other parameters associated with the bG measurement either before or after entry of the bG measurement by the user. For example, the user may be prompted to enter information about how he or she feels; about his or her energy level; about whether a meal was or will be small, medium or large; about the amount of calories and/or carbohydrates of a meal; about whether the user is suffering an illness; or any other information that provides context to the bG measurement. This contextual information is associated with and stored with the bG measurement so that the information can be later recalled and to provide context to the associated bG measurement, assisting the user and others in better managing blood glucose levels.

From step 210 the routine continues at step 212 where a representation of the bG measurement is produced on display 112 by processor 108. In one embodiment, the representation is produced seamlessly on display 112. From step 212 the routine continues at step 214 where the most recently inputted bG value is associated with one or more other bG measurements in its context group. For example, the bG value received at step 210 can be flagged by the user or automatically flagged as a post-prandial or post-exercise bG measurement and then associated with a pre-prandial or pre-exercise bG measurement stored in memory 106. If the user does not wish to display associated bG measurements, or if there is no associated prior bG measurement since, for example, the bG value at step 210 is a pre-prandial or pre-exercise measurement, or the first measurement in a time frame or other episodic context group, and then the routine continues at step 218.

The bG measurement displayed at step 212 can remain displayed while the determination is made at step 214 whether the displayed bG measurement is associated with a prior bG measurement in memory 106. If there is an association with a prior bG measurement, then the routine continues at step 216 where the associated bG values are seamlessly displayed to the user on display 112 via a graphical and/or textual representation. As used herein, a graphical representation may include one or more textual representations in combination with one or more graphical representations of or related to the data. The textual presentation may be included with the graphical presentation, or in one or more alternating displays of the graphical representation. In one embodiment, a graphical representation of the associated bG measurements is produced by processor 108 on display 112 so that the user is provided with a visual representation of the comparison of the associated bG measurements. If display of the associated bG measurements is desired, then the display thereof on display 112 may be produced immediately upon a single user interaction with entry means 114 indicating that the display is desired, or automatically after a pre-determined delay during which the received bG value received at step 210 is displayed. The associated bG measurements processed by bG device 100 and displayed seamlessly to the user can be produced in various forms on display 112 without requiring the user to access and select from various menus or multiple prompts to view the associated bG measurement information. It is also contemplated that the actual bG measurement can be displayed with the graphical representation. The measured bG value can be displayed in the background of display 112, by using a smaller font, or by positioning it at a particular location on the display relative to the graphical representations.

It is contemplated that the graphical and textual representations of the associated bG measurements produced on display 112 by processor 108 include any one or combination of xy-graphs, bar graphs, data plots, pie charts, or other suitable graphical representation to represent the associated bG measurements. In addition, the graphical or textual representations can be color coded to facilitate user interpretation of the results. For example, if one or more of the measured bG values is outside a recommended pre-defined range of blood glucose limits, the display can be presented with a warning indicator or in a warning color, such as red. If the one or more of the measured bG values is near or slightly above or below the pre-defined range of blood glucose limits, the display can be presented with a cautionary indicator or in a cautionary color, such as yellow. If all the associated bG measurements are within the recommended range, then the display can be presented with a satisfactory indicator or color, such as green.

From step 216 the routine continues at either step 218 where the user determines whether to display the bG measurement with its context group of bG measurements or at step 224 where the user can request advice regarding the associated bG measurements of step 216. If the user does not wish to display advice, and proceeds affirmatively at step 218, then processor 108 is programmed or configured to produce a display with a representation of bG measurements in the context group at step 222. The bG measurements in the context group to which the measured bG value was associated are processed so that all or a portion of the bG measurements within that context group are displayed seamlessly to the user in a series of one or more graphical and/or textual representations to provide meaningful bG management information to the user. The seamless display of the bG measurements in the context group on display 112 occurs upon a single user interaction with entry means 114 indicating that the display is desired, or automatically after a pre-determined delay during which the associated bG measurements in step 216 are displayed. The bG measurements in the context group processed by bG device 100 and displayed seamlessly to the user can be produced in various forms on display 112 without requiring the user to access and select from various menus or multiple prompts to view the information.

It is contemplated that the bG measurements in the context group are displayed at step 222 by one or more graphical and/or textual representations on display 112. The graphical and/or textual representations may include any one or combination of xy-graphs, bar graphs, data plots, pie charts, or other suitable representation to represent the bG measurements in the context group. In addition, the graphical and textual representations can be provided with textual representations, messages, indicators and/or color coded to facilitate user interpretation of the result as discussed above.

Examples of the context group representations produced by bG device 100 on display 112 can include trend graphs of bG measurements in the context group over a pre-defined period of time, such as over the last 7 days, over the last 14 days, over the last 30-days, over the last 90 days, or with no day restrictions so that all bG measurements in the context group are displayed. While the actual bG measurements can be displayed graphically at step 222, the bG measurements in the context group can also be processed by processor 108 and displayed at step 222 as a running average of the bG measurements or of average bG measurements over a certain number of days, such as 7, 14, 30 and 90 day averages. The information can also be processed and displayed as measures of variability of the bG measurements, such as maximum-minimum of the bG measurements, the coefficient of variance of the bG measurements, the standard deviation of the bG measurements, or the rate of change of the bG measurements, for example. The bG measurements can also be processed and seamlessly displayed to the user as the Average Daily Risk Range of the bG measurements, estimated HbA1C, or the number of bG measurements within or outside of a pre-defined range or greater or less than a pre-defined threshold. Also, information regarding the compliance with an active testing schedule programmed in the meter can be processed and displayed.

It is further contemplated that at step 222 a number of displays are seamlessly and sequentially produced that include one or a combination of one or more representations of the bG measurements in the context group. For example, a first graphical and/or textual representation of all or a portion of the bG measurements in the context group are produced and displayed, and then a second graphical and/or textual representation of all or a portion of the bG measurements in the context group are seamlessly produced and displayed on display 112. The sequence of seamless displays continues for two or more displays in a pre-arranged sequence so that various bG measurement information in the context group is communicated to the user with minimal or no user interaction with bG device 100 or user entry means 114 to access the series of information. For example, the routine can require that processor 108 first produce and seamlessly display a trend graph, data plot or other graphical representation of bG measurements in the context group over the last 7 days, and then produce and seamlessly display a trend graph for bG measurements in the context group over the last 14 or 30 days, and so forth until the various pre-determined sequence of displays of bG measurements in the context group have been completed or until stopped by the user via entry means 114. It is also contemplated that the use can set up custom sequences of displays on bG device 100 through input to user entry means 114 or through a setup routine that is programmed by, for example, a personal computer and then communicated to and stored in the memory of bG device 100.

From step 216 or step 222, the user also has the option to direct the routine with entry means 114 so that processor 108 analyzes either the associated bG measurements displayed at step 216, or the context group of bG measurements displayed at step 222, to produce a display of useful advice in interpreting and responding to the display of bG measurements. When a request for advice is entered with entry means 114 at step 224, display 112 seamlessly provides a textual representation of the advice to the user at step 228. It is also contemplated that an audible presentation, computer printout, or other suitable communication of the advice could be provided. The advice can indicate whether the associated bG measurements from step 216 or the context group of bG measurements from step 222 are outside a recommended range, within a recommended range, or moderately outside or approaching limits of a recommended range. The advice can also present a recommended action or course of actions to the user based on the bG measurements. For example, if one or more of the bG measurements is severely outside the recommended range, the advice can recommend dietary changes and changes to insulin dosage per a doctor's advice. If one or more of the bG measurements is moderately outside the recommended range, then the advice can recommend dietary changes to assist the user in obtaining future bG measurements within the recommended range. The advice can also provide positive feedback to the user if the bG measurements are within the recommended range and no dietary or insulin dosage changes are needed.

Furthermore, it is contemplated that processor 108 assigns functionality to entry means 114 to provide the user the ability to sequentially cycle back through various sequential displays of the bG measurement data and advice data to an initial display, such as the display of associated bG measurements at step 216 or to the initial display of the context group of bG measurements at step 222. The ability to cycle back through the bG measurement display can assist the user in accessing and further studying a particular data set on display 112 and in obtaining advice relating to those bG measurements in the event the advice was not displayed at the initial opportunity to do so, or if further clarification is needed.

If the user does not wish to display context group bG measurement data or advice at step 224, then the routine continues to step 230 where it returns to step 202 to await a bG measurement. Processor 108 can also be configured so that if the user provides no input of a bG measurement or blood sample for testing for a pre-defined period of time, then power to display 112 of bG device 100 is turned off. If a bG measurement is not to be made at step 202, processor 108 can also be configured to allow the user to access bG measurement data stored in memory 106 and display one or more context groups of bG measurements at step 218. Furthermore, bG device 100 can be accessed without a bG measurement to produce representations of bG measurements in various context groups stored in memory 106 of bG device 100. Such aggregate bG measurement information can be processed and displayed seamlessly to doctors, nurse educators or other interested parties for review without the necessity of a bG measurement to first access the data.

The executable program stored in memory 106 of bG device 100 or operating logic of processor 108 operates processor 108 to seamlessly produce displays on display 112 of information based on one or more bG measurements of a context group as a result of an actual bG measurement and/or a bG measurement recalled from memory 106 of bG device 100. When prompted by the user or after entry of a bG measurement, bG device 100 produces a display of a graphic and/or textual representation of the bG measurement in the context of one or more other bG measurements belonging to the same context group. The display of the representation of the bG measurements in the context group occurs seamlessly with minimal user interface in a single compact device.

In another embodiment of the routine, the user is not queried whether to flag the initial bG measurement at step 204, but rather the bG measurement is automatically associated with its context group based on the set-up of the routine stored in memory 106 or operating logic of processor 108. In this embodiment, flowchart 200 continues from step 202 to step 208 and automatically associates a flag and/or time stamp with the bG measurement to associate it with the appropriate context group.

It is further contemplated that the program installed in memory 106 or operating logic of processor 108 allows the user or other party to provide a setup for bG device 100 that allows the selection of the type of information that shall be displayed seamlessly and in which sequence information shall be displayed. For example, the setup can provide the option of automatic display of the bG measurement with its associated bG measurement in step 216 without user interaction with entry means 114 at step 214. Alternatively or additionally, the setup can provide that each of the displays associated with the bG measurement context group in step 222 or the next message in the advice at step 228 are displayed automatically without user interaction at steps 218 and 224. In this embodiment, the next representation or advice message is displayed on display 112 without any user interaction with entry means 114 or bG device 100 to initiate the display. The setup can also establish the time duration of display for each representation or advice message in the sequence before it is automatically replaced by the next representation or advice message in the sequence. The setup can also allow the user to make a single interaction with entry means 114 so that the user controls the time duration of the display of the bG measurement representation or advice message in the sequence.

The setup routine can be integrated into processor 108 of bG device 100, or into software that runs on a personal computer or from a web site that then transfers the setup of bG device 100 to memory 106 when bG device 100 is connected to the personal computer or web site. The setup routine that runs on the personal computer or web site can be stored in bG device 100 so that it automatically runs when bG device 100 is connected to the personal computer or web site, or the setup can be initiated based on a user input into the personal computer, web site, or bG device 100. The setup routine can allow selection from a number of predefined bG measurement display sequences. The setup routine can also enable the user to define the display sequence and store a custom display sequence of bG measurements in memory 106 of bG device 100 that are later displayed to the user during operation of the routine on processor 108.

Figures 4G, 5G, 6G:
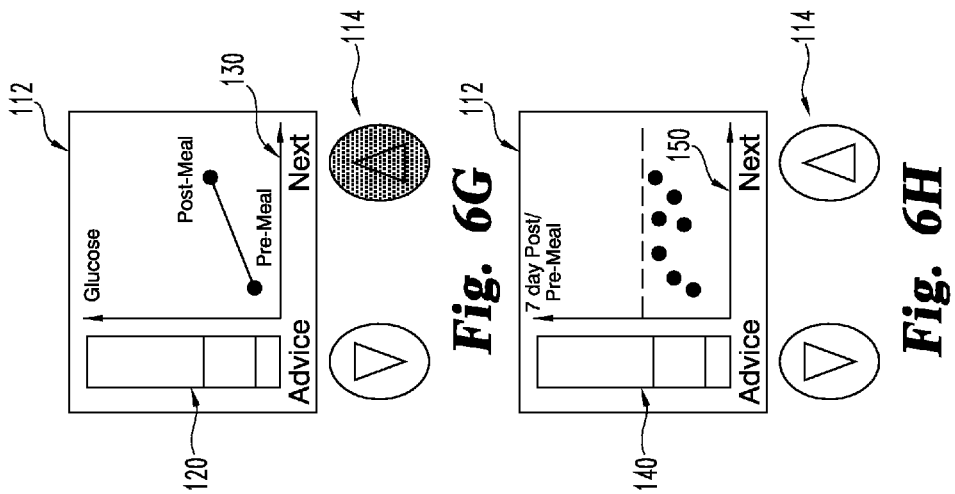
FIGS. 4A-6L illustrate an example of contextually driven user interfaces with sequences of blood glucose management device displays for three different blood glucose measurements.
Figures 4H, 5H, 6H:
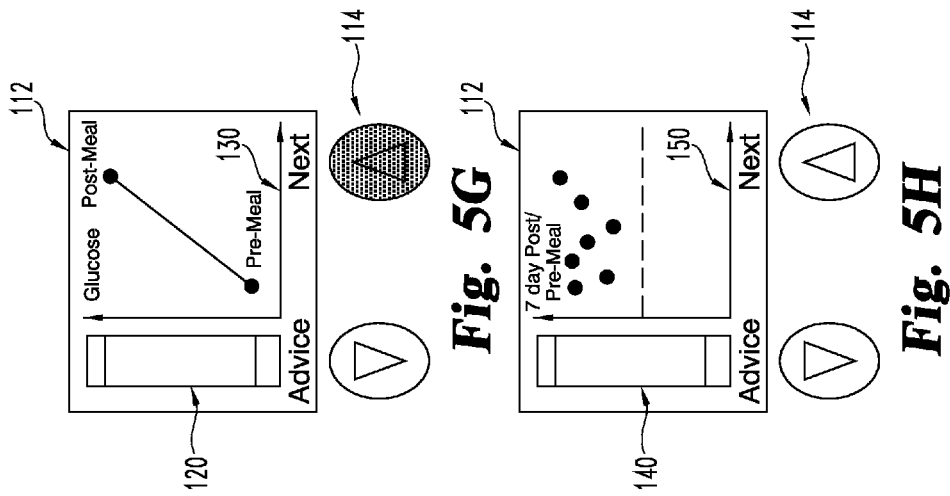

An example of a user interface sequence and operation of a routine or processor represented by flow chart 200 for one context group of bG measurements is depicted in FIGS. 4-6. In this specific example, the context group that drives the specific user interface sequence is given by the association of the measured bG value with a prandial context group of bG measurements. The contextual information displayed relates the actual post-prandial bG measurement to a pre-prandial bG measurement taken earlier by bG device 100 and stored in memory 106.

In operation of bG device 100, either the user or bG device 100 marked a pre-prandial bG measurement and it is stored in memory 106. Furthermore, the user has taken a blood sample and the bG measurement from the sample is supplied to bG device 100. In one embodiment the user has flagged the bG measurements displayed in FIGS. 4A-6A as post-prandial measurement via entry means 114 before or after the actual post-prandial bG measurement is displayed. In another embodiment, processor 108 is configured so that after the user of bG device 100 marks a pre-prandial bG measurement, an alarm or other indicator on bG device 100 audibly or by vibration alerts the user to take the post-prandial measurement after a pre-defined time, such as 90 minutes. The user then performs the recommended post-prandial measurement within the pre-defined time limit and bG device 100 is configured to automatically flag the respective bG measurement as post-prandial. In yet another embodiment, clock 110 of bG device 100 is associated with an electronic scheduler in bG device 100 that alerts the user to perform a bG measurement at specific times of day. Based on the scheduler and the user performing an actual bG measurement within a given time-limit, bG measurements are automatically associated with a pre-prandial or a post-prandial class of measurements in that context group class and flagged as pre-prandial or post-prandial based on the sequence of the bG measurements in the context group. It should be understood that the above descriptions in techniques for flagging and identifying measurements are not limited to prandial measurements, but can also be employed for other measurements in the other context groups discussed herein.

After establishment of the bG measurement as pre-prandial or post-prandial, the user interface on display 112 for the prandial context group is driven by comparing either the post-prandial bG measurement with pre-defined limits or a compound value created by mathematically relating the post and pre-prandial bG measurements to pre-defined limits. The representation of the bG measurements in the example of FIGS. 4A-4L are provided to show an example of bG measurements that are "moderately outside goal range"; the representations of bG measurements in FIGS. 5A-5L provide an example of bG measurements that are "outside of goal range"; and the representations of bG measurements in FIGS. 6A-6L provide an example of bG measurements that are "within goal range".

In each of FIGS. 4-6, entry means 114 includes a left button and a right button with display 112 situated above the buttons. In one embodiment, only two buttons for entry means 114 are provided to simplify user interface and minimize the potential for entry errors. In another embodiment, only three buttons are provided for entry means 114 to simplify user interface and minimize the potential for entry errors. For other embodiments, providing more than three buttons for entry means 114 is not precluded. Processor 108 produces an indication on display 112 of the respective function of each button above the left and right buttons for the particular step in the display sequence of the bG measurement data. A graphical or textual representation of the bG measurement data is also produced on display 112. The buttons of entry means 114 allow the user to seamlessly progress through the sequence of the various displays of data relating to the bG measurement. It should be understood that the buttons in FIGS. 4-6 are for illustration purposes and that entry means 114 may be in any of the forms discussed herein.

In the illustrated example of FIGS. 4A, 5A, and 6A, a bG measurement input to bG device 100 is displayed. The bG measurement is displayed on display 112 with the text "mg/dL" indicating the unit of measure, and the abbreviation "PPG" indicating that the measured bG value belongs to the post-prandial context group. Of course, other abbreviations are contemplated for bG measurements associated with other context groups discussed herein. Display 112 also includes function indicators "Off" and "Graph" at a position that intuitively associates the described function with one of the two buttons of entry means 114. If the user presses the "Off-button", bG device 100 will shut down and no further information is displayed to the user.

If the user presses the "Graph" button of entry means 114, as indicated by the shaded button in FIGS. 4A-6A, processor 108 seamlessly produces a graphical representation on display 112 of the associated pre-prandial and post-prandial bG measurements stored in memory 106, as indicated in FIGS. 4B-6B. Examples of contemplated representations on display 112 include a bar-graph element 120 and a xy-graph element 130, among others. In addition, the buttons of entry means 114 are assigned new functions, which are indicated to the user by displaying "Advice" and "Next" above the respective buttons. The height of bar graph element 120 indicates the difference between the pre- and post-prandial bG measurements. Furthermore, bar graph element 120 may include coloration or other suitable indicator to indicate whether the post-prandial measurement is "moderately outside goal range" (FIG. 4B); "outside of goal range" (FIG. 5B); or "within goal range" (FIG. 6B). The color indicators can include a yellow color for bar graph element 120 in FIG. 4B; a red color in FIG. 5B; and a green color in FIG. 6B. In addition, xy-graph element 130 shows both the pre- and post-prandial bG measurements in a xy-line chart, where the y-axis represents the glucose concentration of the bG measurements and the x-axis represents time or sequence of the bG measurements. Other information may also be displayed on display 112 with graph elements 120, 130 such as, for example, the value of the post-prandial bG measurement of FIGS. 4A-6A.

In FIGS. 4C-6C, the same display as in FIGS. 4B-6B is shown, but the user presses the "Advice" button as indicated by shading to seamlessly advance to an advice sequence. FIGS. 4D-6D are a textual representation of advice that is produced by processor 108 on display 112 based on an interpretation of the bG measurements relative to pre-defined limits. In addition, display 112 indicates the functionality assigned to the buttons of entry means 1 14. One of the buttons is assigned a "Back" function that allows the user to go back to the display sequence of FIGS. 4B-6B. The other button is assigned a "Next" function. In FIGS. 4E-6E, the user presses the "Next" button, as indicated by its shading, to seamlessly display additional advice relating to the bG measurements. As shown in FIGS. 4F-6F, the next display of advice on display 112 provides recommended dietary and insulin changes based on the bG measurement relative to the pre-defined limits (FIGS. 4F-5F), or the advice on display 112 can provide positive feedback to the user if the bG measurements are within the pre-defined limits (FIG. 6F). Furthermore, FIGS. 4F-6F illustrate the indication on display 112 of new functions assigned to the buttons of entry means 114. In the illustrated example, one of the buttons is assigned a "Back" function to allow the user to sequence back to the display of FIGS. 4D-6D, and the other button is a dead key indicating that no further advice is available. Of course, the advice display sequence is not limited to two display screens, and it is contemplated that the advice sequence can include a single display screen in the sequence, or more than two display screens in the sequence. From the display in FIGS. 4D-6D, the user can press the "Back" button again to cycle to the display in the sequence with the initial graphical representation of the associated bG measurements in FIGS. 4B-6B.

From the display of FIGS. 4B-6B, the user can opt to display additional graphical and/or textual representations of the bG measurements in the context group with a press of the button associated with the "Next" function, as indicated by the shading of the "Next" button in FIGS. 4G-6G. In FIGS. 4H-6H, graphical representations of the pre-prandial and post-prandial bG measurements over the last seven days are produced and seamlessly displayed in a bar graph 140 and a xy-graph 150. The bar graph 140 can be shown in a different color based on the whether or not an acceptable number of the bG measurements over the last seven days are within, well within, or outside pre-defined limits. The current bG measurement in the xy-graph can be highlighted by a different color or shape (not shown). The y-axis of the xy-graph can represent the actual bG measurements, difference between associated bG measurements, the ratio of associated bG measurements, or another appropriate mathematical function of the associated pre-prandial and post-prandial bG measurements. The x-axis represents time or a sequence in time of the bG measurements. The xy-graph may also show a dashed line extending from the y-axis parallel to the x-axis to indicate a boundary of the goal range.

The display of bG measurements in the context group in FIGS. 4H-6H also includes textual indicators above respective buttons of entry means 114 to indicate the respective functions to the user. For example, one of the buttons is assigned an "Advice" function that, when pressed as shown by shading in FIGS. 4I-6I, displays advice based on an interpretation of the bG measurements in the context group over the last seven days, as shown in FIGS. 4J-6J. From the display in FIGS. 4J-6J, the user can cycle back to the previous display by pressing the button assigned the "Back" to access the display of FIGS. 4H-6H.

From the display in FIGS. 5H-6H, the user can press the button of entry means 114 assigned the "Next" function, as indicated by shading in FIGS. 4K-6K, in order to produce and seamlessly display the next graphical representation of the bG measurements in the context group, as shown in FIGS. 4L-6L. In FIGS. 4L-6L, the graphical representations of the context group data include thirty days of bG measurements displayed graphically in a bar graph 160 and xy-graph 170. The xy-graph 170 provides a representation of the bG measurements over the last 30 days along with a trending line that indicates the trend of the bG measurements over the last 30 days. From the display sequence in FIGS. 4L-6L, the user is provided with the option to seamlessly access advice based on an interpretation of the 30 day bG measurements, or to display another graphical representation of the bG measurements in the context group. The graphical and advice display sequences can continue to display additional information relating to bG measurements in the context group depending on the pre-defined parameters provided in the setup of the routine in bG device 100.

In the display sequences of FIGS. 4-6, when no button press occurs within a pre-determined time limit, bG device 100 will automatically shut off. Auto shutoff can occur at any point in the sequence if no user interaction is registered by bG device 100 for a pre-defined period of time to save battery life. The user interface sequence shown in FIGS. 4 to 6 provides an example of the seamless display of information regarding associated bG measurements and bG measurements in the context group in addition to the actually measured bG value. It should be understood, however, that the present invention is not limited to the specific examples of bG measurements, associated bG measurements, context group and advice illustrated herein.

Figure 7:
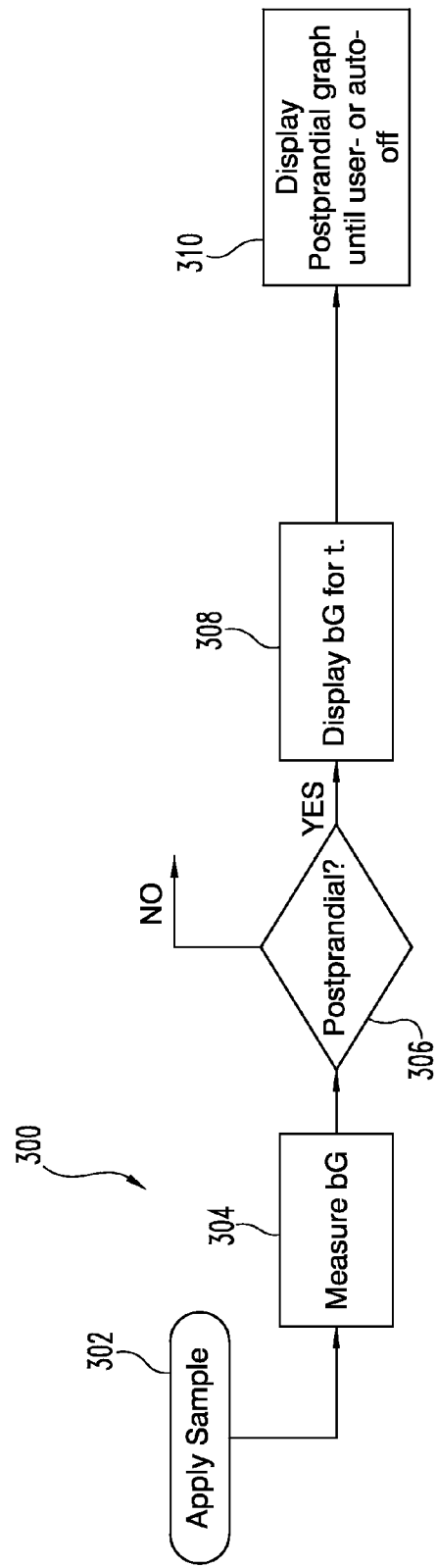
FIG. 7 is a flow chart illustrating steps of an embodiment of a routine includable in the blood glucose management device of FIG. 1 to seamlessly display graphical representations of blood glucose measurements.

Another embodiment of an operation of processor 108 or program to operate processor 108 of bG device 100 is shown in flow chart 300 in FIG. 7. Flow chart 300 starts at step 302 where a blood sample is input to bG device 100 by, for example, user provided data or from test strip port 118. At step 304 the bG value is measured to provide a bG measurement. At step 306 it is determined whether the bG measurement is post-prandial, by any one or combination of a user flag, automatic determination based on the time of day of the measurement, by an electronic schedule, or the sequence of previous bG measurements stored in memory 106. If the bG measurement is determined to not be post-prandial at step 306, then the user can be provided with the option to produce a graphic representation of the bG measurements in the context group stored in memory 106. If, for example, the bG measurement is post-prandial, the bG measurement is marked as a post-prandial value and the bG measurement is displayed to the user on display 112 at step 308. After a predefined period of time t (such as 3 seconds or another predefined period of time), processor 108 automatically produces a graphical representation of the associated pre-prandial and post-prandial bG measurements on display 112 at step 310, such as shown in FIGS. 4B-6B, without any input from the user via entry means 114. The associated bG measurements are displayed for a predetermined time t, and then processor 108 automatically advances the sequence to produce the next graphical representation on display 112, such as shown in FIGS. 4H-6H, without any user entry from input means 114. Accordingly, the various graphical representations in the display sequences occur seamlessly and without any user interaction with input means 114. Furthermore, it is contemplated that textual representations may be produced with the graphical representations.

In the embodiment of FIG. 7, buttons or other entry features of entry means 114 may not be assigned functions as the screens advance through the display sequence. However, the assignment of one or more functions to entry means 114 and display of these functions on display 112 is not precluded. For example, one or more of the buttons may be assigned an "Advice" function so that the user can seamlessly access advice information for the particular bG measurement data currently displayed. One or more buttons may also be assigned "Next" and "Back" functions so the user has the option to override the automatic display sequence of the bG measurement data. If a plurality of advice displays are available for a particular bG measurement display, the various advice displays can automatically advance from one advice display to the next unless stopped by the user with entry means 114. The user can also cycle back through the advice displays to the last displayed bG measurement graphical representation and interact with entry means 114 to initiate automatic display of any remaining graphical representations of the bG measurement data that might be available.

In another embodiment shown in FIGS. 8A-8E, bG device 100 is programmed with a routine or configured with operating logic that allows the patient, doctor, nurse or other user to seamlessly access and display summary measurement data of bG measurements in the various context groups stored in memory 106. In FIGS. 8A-8E, bG device 100 is shown in operation with entry means 114 adapted to provide a means for inputting a request to processor 108 to initiate the display of summary measurement data of bG measurements. In FIG. 8A, input 114' of entry means 114 is engaged, as indicated by its shading, by the user to seamlessly display the summary measurement data for the bG values in the various pre-defined context groups over a pre-defined time period. For example, the illustrated embodiment shows the bG measurements in their respective context groups in an xy-graph over a thirty day time period along the x-axis and representations of the bG measurements along the y-axis. In FIG. 8B, the summary measurement data for the fasting context group is produced on display 112. After a period of delay of time t, the next context group of pre-prandial and post-prandial summary measurement data is produced and seamlessly displayed to the user in FIG. 8C. After another period of delay of time t, the next context group of summary measurement data showing the Average Daily Risk Ratio of the bG measurements is produced and seamlessly displayed to the user in FIG. 8D. After another period of delay of time t, the next context group of summary measurement data for predicted HbA1c is produced and seamlessly displayed to the user in FIG. 8E.

Various components of entry means 114 can be assigned various functions to facilitate the sequencing and seamless display of the summary measurement data. For example, with a three button entry means 114, one of the buttons, such as the middle button, can be used to initiate the summary measurement data display sequence, and can also be used to pause and re-start the automatic display of the summary measurement data display sequence as indicated by the pause symbol on display 112 in FIGS. 8B-8E. Another of the buttons, such as the left button, can seamlessly move the display sequence back to a previous display screen as indicated by the back arrow on display 112. Another of the buttons, such as the right button, can move the display sequence forward to seamlessly display the next display screen in the sequence as indicated by the forward arrow on display 112. Automatic display of the summary measurement data can be resumed by engaging the middle button.

The summary data display routine illustrated in FIGS. 8A-8E presents summary measurement data from bG measurements in their various context groups and seamlessly displays this information on bG device 100 to the user. This information can be used by the patient, doctors, nurse educators or other interested parties for review to facilitate understanding and interpretation of the bG measurements in aggregate in the various context groups while minimizing the number of user interactions with bG device 100 in order to access this aggregate data. Furthermore, the information presented in FIGS. 8A-8E could also be sent to a printing device or personal computer that is connected to bG device 100 by either wired or wireless transmission. Such a print-out or data transmission sequence might be initiated by a press-and-hold of one of the buttons of entry means 114, such as the button 114' that is used to initiate the summary measurement data display sequence.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A portable blood glucose management device, comprising:
 a housing including a display and a user entry means for receiving user input;
 a processor in the housing operatively connected to the display and the user entry means; and
 a memory connected with the processor,
 wherein the processor is configured to:
 produce on the display a representation of a blood glucose measurement that may be stored in the memory,
 associate the blood glucose measurement with at least one other blood glucose measurement that may be stored in the memory to obtain associated blood glucose measurements, and
 seamlessly produce on the display a graphical representation of the associated blood glucose measurements for a period of time automatically and without user input to the user input means after producing the representation of the blood glucose measurement, and
 wherein the processor is further configured to:
 associate the blood glucose measurement and a plurality of blood glucose measurements in the memory with a context group in the memory, and seamlessly and sequentially produce on the display a plurality of graphical representations of blood glucose measurements in the context group for a period of time automatically and without user input to the user input means after producing the graphical representation of the associated blood glucose measurements.

2. The device of claim 1, wherein the processor is further configured to seamlessly produce on the display advice directed to a currently displayed one of the graphical representations upon user input into the user entry means.

3. The device of claim 2, wherein the advice includes an interpretation of the blood glucose measurements in the currently displayed graphical representation relative to pre-defined blood glucose limits.

4. The device of claim 3, wherein the advice includes a recommended dietary change.

5. The device of claim 2, wherein the user entry means includes at least two buttons, and the user input consists of one press of one button of the user entry means.

6. The device of claim 1, wherein the plurality of graphical representations includes xy-graphs of blood glucose measurements in the context group for at least one of a seven day time period and a thirty day time period.

7. The device of claim 1, wherein the entry means includes at least two buttons located adjacent to the display, and further wherein the processor is configured to assign a function to each of the at least two buttons and to produce the assigned functions on the display, and wherein the assigned functions depend on the graphical representation being currently produced on the display.

8. The device of claim 1, wherein the context groups include at least two or more of a fasting context group, a prandial context group, an exercise context group, a pre-sleep context group, an episodic testing context group, a pre-office visit context group, a glucose tolerance context group, an Average Daily Risk Ratio context group, and a predicted HbA1c context group.

9. The device of claim 1, wherein the device further comprises a test strip port formed in the housing for receiving a test strip, wherein the blood glucose measurement comprises the result from a measurement performed on a blood sample provided to a test strip received within the test strip port, the processor being operable to perform said measurement and to store the blood glucose measurement in the memory.

10. The device of claim 1, wherein the device further comprises a data communications port in the housing, wherein the blood glucose measurement comprises a measurement result transferred from a second device and through the communications port, the processor being configured to receive the transferred result and to store the result in the memory as the blood glucose measurement.

11. The device of claim 1, wherein processor is configured to selectively pause and resume the seamless and sequential display of the graphical representations upon user input to the user entry means.

12. A method for displaying blood glucose measurements, comprising:
inputting a blood glucose measurement into a blood glucose management device, wherein the blood glucose management device comprises:
a housing including a display and a user entry means for receiving user input;
a processor in the housing operatively connected to the display and the user entry means; and
a memory connected with the processor;
displaying the blood glucose measurement on the display of the blood glucose management device;
associating via the processor, the blood glucose measurement with at least one other blood glucose measurement stored in the memory of the blood glucose management device to obtain associated blood glucose measurements;
seamlessly displaying a graphical representation of the associated blood glucose measurements on the display of the blood glucose management device for a period of time automatically and without any user interaction with the user entry means of the blood glucose management device after displaying the blood glucose measurement;
associating via the processor, the blood glucose measurement with at least one context group of a plurality of blood glucose measurements stored in the memory of the blood glucose management device; and
seamlessly and sequentially displaying a sequence of a plurality of graphical representations of blood glucose measurements in the at least one context group on the display of the blood glucose management device for a period of time automatically and without any user interaction with the user entry means after displaying the graphical representation of the associated blood glucose measurements.

13. The method of claim 12, further comprising seamlessly displaying a sequence of a plurality of graphical representations of blood glucose measurements in a plurality of context groups of blood glucose measurements stored in the memory of the blood glucose management device each for a period of time automatically and without any user interaction with the user entry means.

14. The method of claim 13, wherein the context groups are segregated based on a time of day of the blood glucose measurements associated therewith.

15. The method of claim 12, further comprising assigning and displaying at least two functions to user entry means of the blood glucose management device while seamlessly displaying the graphical representation of the associated blood glucose measurements.

16. The method of claim 15, wherein one of the at least two functions provides an input to seamlessly display advice regarding the associated blood glucose measurements and the other of the at least two functions provides an input to seamlessly display a second graphical representation of the blood glucose measurement with an associated context group that includes a plurality of blood glucose measurements over time stored in the blood glucose management device.

17. The method of claim 16, wherein the advice includes at least one of an interpretation of the blood glucose measurements relative to pre-defined blood glucose limits and a recommended dietary change.

18. The method of claim 12, further comprising the steps of:
storing a plurality of blood glucose measurements in the memory of the blood glucose management device;
associating each of the plurality of blood glucose measurements with at least one of a number of context groups stored in the memory of the blood glucose management device; and
seamlessly displaying on the blood glucose management device a sequence of at least one graphical representation of each of the number of context groups with its associated blood glucose measurements each for a period of time automatically and without any user interaction with the user entry means after a current graphical representation is displayed for a period of time.

19. The method of claim 18, wherein seamlessly displaying the sequence of at least one graphical representation of each context group can be paused by pressing a button on the blood glucose management device.

\* \* \* \* \*